United States Patent [19]

Han

[11] Patent Number: 4,631,258
[45] Date of Patent: Dec. 23, 1986

[54] IRRADIATION ALCOHOL FERMENTATION PROCESS

[75] Inventor: Youn W. Han, New Orleans, La.

[73] Assignee: The United States of America as represented by the Secretary of Agriculture, Washington, D.C.

[21] Appl. No.: 524,178

[22] Filed: Aug. 17, 1983

[51] Int. Cl.⁴ .......................... C12P 19/14; C12P 7/06
[52] U.S. Cl. ...................................... 435/99; 426/11; 435/161; 127/71
[58] Field of Search .................... 435/161, 99; 426/11; 127/71

[56] References Cited

U.S. PATENT DOCUMENTS 4,115,146  9/1978  Saint-Lebe et al. .................. 127/71

OTHER PUBLICATIONS

Matsumoto, N., Fukushi, O., Miyanaga, M., Kakihara., Nakajima, E., and Yosjozumi, H.; "Industrialization of a Noncooking System For Alcohol Fermentation From Grains"; *Agri. Biol. Chem.* 46(6) 1549-1558 (1982).

Ueda, S., Zenin, C. Y., Monteiro, D. A., and Park, Y. K.; "Production of Ethanol From Raw Cassava Starch By a Nonconventional Fermentation Method"; *Biotechnol. Bioeng.* 23, 291-299 (1981).

Abd Allah, M. A., Foda, Y. H. and El Saadany, R., "Effect of Gamma Rays On Starch Extract From Irradiated Wheat Flour"; *Die Starke* 26, 89-93 (1974).

Watanabe, Y.; "Gamma Irradiation of High Amylase Corn Starch"; *J. Jap. Soc. Starch Sci.* 24, 240-249 (1978).

AnanthaswaMY, H. N., Vakil, U. K. and Sreenivasan, A. "Effect of Gamma Radiation On Wheat Starch and Its Components"; *J. Food Sci.* 35, 795-798 (1970).

Saadany et al.; "Degredation of Corn Starch Under The Influence of Gamma Irradiation" *Die Starke* 28, 208-211 (1976).

Rose-Economic Microbiology vol. 1 (Alcoholic Beverages) 1977 (Academic Press) pp. 656-659.

*Primary Examiner*—Sam Rosen
*Attorney, Agent, or Firm*—M. Howard Silverstein; David G. McConnell; Raymond C. Von Bodungen

[57] ABSTRACT

An alcohol fermentation process which eliminates the heat gelatinization process is disclosed. Corn is irradiated with about $10^5$ to $10^7$ rads of gamma radiation to effect sugar yield, susceptibility to enzymatic hydrolysis of starch, yeast growth, and alcohol production. The irradiated corn is then treated with amylases complex, yeast fermented and distilled into alcohol.

4 Claims, 1 Drawing Figure

IRRADIATION ALCOHOL FERMENTATION PROCESS

FIELD OF THE INVENTION

This invention deals with a novel irradiation process for alcohol fermentation.

DESCRIPTION OF THE PRIOR ART

Because of the foreseeable shortage of the worlds fossil fuel supply and its ever increasing price, much attention has been paid to the use of alcohol as an alternative energy source. However, with present technology, alcohol production from starch materials is not economical because of the great energy requirements in cooking, sterilization and distillation processes. Industrial production of alcohol from cereal grains such as corn is usually done by cooking the mash at a high temperature of nearly 140° C. prior to saccharification and fermentation. The mash is cooked to rupture the structure of the grain grits to elute starch for enhanced liquefaction and saccharification by amylases and also to sterilize the mash. The energy-intensive cooking process contributes to the unfavorable economics of the present alcohol fermentation process.

Several attempts have been made to reduce or eliminate the heat requirement in the cooking process by using black koji amylase which reportedly digests raw starch. See Matsumoto et al.; "Industrialization of a Noncooking System for Alcohol Fermentation from Grains", *Agri. Biol. Chem.* 46(6) 1549–1558 (1982) and Ueda et al.; "Production of Ethanol from Raw Cassava Starch by a Nonconventional Fermentation Method", *Biotechnol. Bioeng.* 23, 291–299 (1981). Fermentation efficiency was equal or superior to that of the high temperature cooking system.

Starch substrates have been treated with high energy radiation to alter their structure and properties. See Abd Allah et al., "Effect of Gamma Rays on Starch Extract from Irradiated Wheat Flour", *Die Starke* 26, 89–93 (1974) and Ed Saadany et al, "Degradation of Corn Starch under the Influence of Gamma Irradiation", *Die Starke* 28, 208–211 (1976). The high energy radiation resulted in degradation of starch molecules, increased reducing sugar and enzyme digestibility, and decreased viscosity of the treated materials. However, none of the prior art teaches uses for eliminating the heating step prior to fermentation.

Watanabe, Y; "Gamma Irradiation of High Amylase Corn Starch"; *J. Jap. Soc. Starch Sci.* 25, 240–249 (1978) compared the properties of insoluble residues from irradiated starches with non-irradiated starch and reported that the starch granules were destroyed at random in both the crystalline and amorphous form by gamma irradiation.

Ananthaswamy et al; "Effect of Gamma Radiation on Wheat Starch and its Components", *J. Food Sci.* 35, 795–798 (1970) reported that radiolytic breakdown products of starch irradiated at one Mrad were mainly maltose and maltotetrose thereby resembling products produced by o-amylosis of starch.

SUMMARY OF THE INVENTION

A process which eliminates the heating step in alcohol fermentation processes is disclosed. Applicant demonstrates that it is possible to completely eliminate this heating step by treating corn with gamma radiation prior to saccharification and fermentation. Gamma irradiation at sufficient dosage greatly enhances the alcohol yield by subsequent yeast fermentation of the treated corn. Applicants irradiation process demonstrates an alcohol yield almost equivalent to that from fermentation of cooked (gelatinized) corn. Thus, the cooking process in conventional fermentation of starch-based substrates can be eliminated by gamma irradiation.

Cracked corn was irradiated with sufficient amounts of gamma radiation to affect sugar yield, susceptibility to enzymatic hydrolysis of starch, yeast growth, and alcohol production.

About 12% reducing sugar was produced by amylase treatment of uncooked, irradiated (50–100 Mrad) corn. This amount exceeded the level of sugar produced from cooked (gelatinized) corn by the same enzyme treatment. Yeast numbers in submerged cultivation was higher on a corn substrate that was irradiated at $10^5$–$10^7$ rad compared to that on an unirradiated and cooked corn. About the same level of alcohol was produced on uncooked, irradiated corn as corn. Therefore, the conventional cooking process for gelatinization of starch prior to its saccharification can be eliminated by irradiation. Irradiation also eliminates the necessity of sterilization of the medium and reduces the viscosity of high levels of substrate in the fermentation broth.

DESCRIPTION OF THE PREFERRED EMBODIMENTS

Materials and Methods

Figure 1:
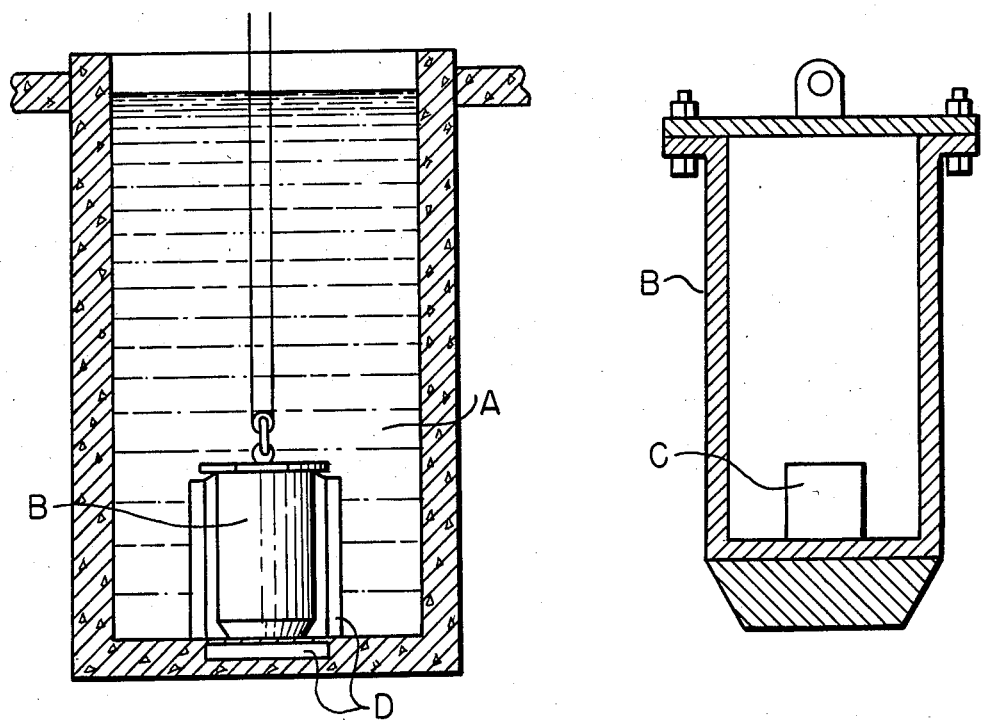

Substrate:
  Cracked corn.
Enzymes:
  $\alpha$Amylase (B. subtlis, 25 U/mg, U.S. Biochemical Corp), $\beta$-amylase (Barley, 12 U/mg, Sigma Chemical), amyloglucosidase (Rhizopus, 10 U/mg, Sigma Chemical) were used. One g of $\alpha$-amylase, 0.5g of $\beta$-amylase and one g of amyloglucosidase were dissolved in 30 ml of distilled water and one ml of the enzyme mixture was added into 100 ml of fermentation broth that contained different amounts (10%, 15%, and 30%, w/v) of substrate. The enzyme substrate mixture was held one hr at 50° C. before yeast inoculation. Prior to enzymatic hydrolysis irradiated corn was cooked for 30 min at 121° C. to gelatinize the starch.

Organism and fermentation:
  *Saccharomyces cerevisiae* (NRRL Y-2034) was used for alcohol fermentation. The organism was grown on malt extract and maintained on a potato dextrose agar. Actively growing yeast was harvested by centrifugation and resuspended in distilled water. One ml of yeast suspension was inoculated into 100 ml of fermentation broth in a 120 ml bottle. Cracked corn irradiated at 0, $10^5$, $10^6$, $10^7$, $5\times10^7$, and $10^8$ rad was mixed with tap water and the pH of the mixture adjusted to 3.5 with 42% $H_3PO_4$. The treated corn was divided into three parts: (1) untreated control, (2) treated with amylases without cooking, and (3) heated at 121C for 30 min and treated with the amylases. The amylase mixture contained the three enzymes listed in the enzyme section. The fermentation was carried out with three different substrate levels (10, 15, and 30%, w/v) at 30C on a rotary shaker (150 rpm) for the first 24 hr and kept still for the next three days with only occasional agitation. The level of yeast growth in submerged cultivation was determined by a plate count on the fermentation broth in which yeast had been cultivated for 3 days at 30° C.

on a rotary shaker (150 rpm). The fermentation broth, pH 6.5, contained 10 g corn in 100 ml tap water.

Gamma source and irradiation:

About one kg of cracked corn was packed in closed glass containers at the prevailing moisture condition (about 15% w/w). Containers were sealed under ambient conditions without excluding air and placed in a cast aluminum basket. Samples were then subjected to gamma irradiation at dosages of 0 to 100 Mrd. Irradiation was performed in a watershield Co-60 gamma cell that produced a dosage of approximately 2000 rd/min. A schematic diagram of the irradiation facility is shown in FIG. 1 wherein (A) is water, (B) is irradiation basked, (C) sample and (D) is a cobalt 60 source. Because the radiation source capsule was placed in a swimming pool and the samples were irradiated under water, no extra safety precaution was needed for radiation leakage. Also, there was no special problem in handling the irradiated materials, as the energy level of the gamma source (1.33 MeV) was far less than the energy required for activation of the material (5–10 MeV).

Analytical procedures:

The amount of reducing sugar was determined by the dinitrosalicylic acid (DNS) method while glucose was measured by the glucose oxidase/peroxidase system (Sigma Technical Bulletin, No. 510). Alcohol was determined by a gas chromatograph equipped with a Tenax GC column (8% polymethaphenyl ether, Ni-200, 10 ft × ⅛ inch) and with a flame ionization detector. Two microliters of each sample with a standard response factor of 384,620 integrator counts per microgram ethanol was injected, allowed two min to vaporize (injection port 220° C.), and the column programmed from 90° C. to 180° C. at 8° C./min (2 min hold). The level of alcohol was calculated on a volume per total volume basis (ml/100 ml).

Water soluble acidity was determined by titrating the water extractibles of irradiated corn. One g of irradiated corn was mixed in 100 ml of water and shaken for 1 hr at room temperature. The mixture was filtered through Whatman No. 1 filter paper and an aliquot diluted and titrated with 0.01N NaOH. The acidity was calculated as mg $CH_3COOH$ per 100 g corn.

Iodine affinity of starch was measured as follows: One gram of irradiated corn was ground to pass a ¼ inch screen and then suspended in 10 ml of water and shaken for 1 hr. The supernatant was diluted 100 fold and to it was added one ml of an iodine solution that contained 20 g KI and two g $I_2$ per liter of water. The blue color developed was measured by reading optical density at 580 nm.

The following examples set forth the preferred embodiments of the invention:

EXAMPLE 1

About one Kg of cracked corn was packed in a glass container at prevailing moisture conditions (about 15%, w/w). The containers were sealed under ambient conditions without excluding air and placed in a cast aluminum basket. Samples were then irradiated at 0, $10^5$, $10^6$, $10^7$, $5 \times 10^7$, and $10^8$ rad. Irradiation was performed in a watershield Co-60 gamma cell that produced a dosage of approximately 2000 rad/min. The irradiated corn was mixed with tap water and the pH of the mixture adjusted to 3.5 with 42% $H_3PO_4$.

Such treated corn was divided into three parts for alcohol fermentation for comparison: (1) untreated control, (2) treated with amylases without heating, and (3) heated at 121° C. for 30 min and treated with amylases. The enzyme treatment consisted of adding a mixture of alpha amylase (833 U), B-amylase (200 U) and amyloglucosidase (333 U) to 30 g corn in 100 ml water and holding the enzymesubstrate mixture in 50° C. water bath for one hour with occasional shaking. Fermentation broth contained 10 g of such treated corn and 100 ml of water in 120 ml containers.

One ml of actively growing yeast was inoculated into each container of fermentation broth and the fermentation was carried out at 30° C. on a rotary shaker (150 rpm) for the first 24 hours and then kept still for the next three days with occasional agitation. Triplicate samples were prepared and fermented and the average of the three analyses were reported in Table 6.

At the end of fermentation, the sample irradiated at $10^5$ to $10^6$ rad and amylases treated produced 3.51 to 3.79% (w/v) of alcohol while the sample that was not irradiated but heated (121° C. for 30 min) and enzyme treated produced 3.28% (v/v) alcohol. Samples that was not irradiated and not treated with enzyme produced far less (1.24%) alcohol.

EXAMPLE 2

In a similar experiment, where all the experimental conditions were the same as that in Example 1 except for the high initial substrate level, a similar pattern of alcohol production was observed. On fermentation of corn (15%, w/v) that was irradiated ($10^5$ to $10^6$ rad) and amylase treated produced 3.30 to 3.68% (v/v) of alcohol whereas the corn that was heated (unirradiated) and amylase treated produced 3.89% alcohol. Unheated and unirradiated sample produced only 2.46% alcohol.

A similar result was repeatedly obtained for even higher initial substrate (30%, w/v). Fermentation of 30% corn (initial substrate level in the fermentation broth) produced 4.56 to 7.35% alcohol from the sample irradiated $10^5$ to $10^6$ rad) and amylase treated while 7.76% alcohol was produced from the heat treated (unirradiated) and amylase treated sample. Unheated and unirradiated sample produced 4.40% alcohol.

In all experiments, the level of alcohol produced by irradiation and heat treatment followed by enzyme treatment and yeast fermentation was about the same. It is thus apparent that the effect of irradiation in rendering the starch substrate for saccharification and alcohol fermentation is about the same as that for heat treatment (gelatinization).

EXAMPLE 3

To substantiate the beneficial effect of gamma irradiation in alcohol production, the level of yeast growth or irradiated and unirradiated corn was compared. The level of yeast growth was determined by a plate count on the fermentation broth in which yeast had been cultivated for three days at 30° C. on a rotary shaker (150 rpm). The fermentation broth, pH 6.5, contained 10 g corn and 100 ml tap water.

As shown in Table 3, the number of yeast cells grown on corn that was irradiated $10^5$ to $10^6$ rad) and amylase treated was $34 \times 10^7$/ml whereas the number of yeast on the sample that was heated (irradiated) and enzyme treated was $21 \times 10^7$ cells/ml. The number of yeast cells on the unirradiated and unheated sample was $20 \times 10^7$ cells/ml. The higher number of yeast cells in the irradiated sample favored the alcohol production.

RESULTS AND DISCUSSION

Gamma irradiation significantly increased the susceptibility of corn to enzymatic hydrolysis (Table 1). Enzymatic hydrolysis of the corn, uncooked and irradiated at 50 Mrd, produced about 12% of reducing sugar. This amount exceeded the level of sugar produced from the corn that was cooked but not irradiated. Gamma irradiation also increased the digestibility of cooked corn. However, the degree of increase was much greater for uncooked corn (226%) than cooked corn (94%). About 3.7% and 6.1% of reducing sugar were produced in the corn irradiated at 50 Mrd and 100 Mrd, respectively.

The pattern of glucose production by amylases from irradiated corn was similar to that for reducing sugar production i.e., when treated with a mixture of α-amylase, β-amylase and amyloglucosidase, about 2–3 times more glucose was produced from the corn irradiated at 50 to 100 Mrd than from the untreated control (Table 2). A similar effect was also noted on the corn irradiated and treated with amyloglucosidase, whereas α-amylase and β-amylase produced little glucose regardless of the irradiation dose. Therefore, an irradiation dose of 50 Mrd or greater significantly increases the digestibility of corn by amylogucosidase. Although the reducing capacity of starch was increased after irradiation, very little glucose was found in the degradation products.

Yeast growth on corn substrates subjected to different doses of gamma radiation was compared (Table 3). Yeast growth in submerged cultivation was lower on a corn substrate that was irradiated at 50 Mrd or greater compared to the unirradiated corn. The inhibition of yeast growth was especially noticeable on corn that was irradiated at 50 Mrd or greater and not treated with the enzyme. This probably results from the generation of harmful products in the irradiated material. About the same level of yeast growth was observed on uncooked and amylase treated corn as the cooked and amylase treated corn, whereas the yeast growth on totally untreated corn was considerably lower.

Treatment of corn with gamma rays degraded the starch molecules as indicated by the reduction in iodine uptake of the treated sample (Table 4). The effect was apparent at 50 Mrd dosages or greater with almost complete destruction of starch occurring at 100 Mrd. Destruction of starch molecules by gamma irradiation was also indicated by polarizing light microscopy. Unirradiated starch granules immersed in water were strongly birefringent whereas, birefringency diminished as the dosage of irradiation increased until it appeared to vanish in samples treated with 100 Mrd. Examination of dry samples indicated that all of the specimens, even those subjected to 100 Mrd irradiation, were birefringent but that water dissolved the contents of strongly irradiated granules. Inspection of starch granules immersed in oil showed that granules treated with high dosages of irradiation tended to be less intensely birefringent than those treated with lower dosages. Observation of the starch granules in the scanning electron microscope, which only shows surface topography, failed to reveal any differences among the various treatments.

A considerable amount of acid was formed upon irradiation of corn (Table 5). Since the energy from gamma rays randomly cleaves the starch molecule, a variety of compounds including sugar acids, deoxysugars, malonealdehyde, dehydroxyacetone and low molecular weight products such as $H_2O$, $CO$, $CO_2$, $H_2$, $HCHO$, $HCOOH$ were expected to form.

The effect of gamma irradiation and cooking (gelatinization) of starch on alcohol yield by fermentation was compared. The alcohol fermentation was run with 10, 15, and 30% levels of corn that had been previously irradiated at 0 to 100 Mrd. The data (Table 6) from the three substrates invariably showed that gamma irradiation significantly increased the alcohol yield and that the conventional cooking process for gelanization of starch prior to its saccharification could be eliminated by gamma irradiation. The uncooked corn which was irradiated at about one Mrd produced almost as much alcohol as that from gelatinized and unirradiated corn. For example, at the 30% substrate level, the irradiated ($10^6$ rd) and uncooked corn produced 7.35% alcohol whereas the unirradiated cooked (gelatinized) corn produced 7.76% alcohol. The alcohol yield was also increased for both uncooked corn (67%) and cooked corn (21%) by gamma irradiation at about one Mrd. However, further irradiation beyond one Mrd decreased the alcohol yield, probably as a result of the presence of harmful products resulting from irradiated. Added advantages of gamma irradiation include the elimination of the necessity of sterilization of the fermentation broth as well as enabling the loading of high levels of substrate by reducing the viscosity of the medium. A high level substrate is essential for production of high yields of alcohol.

TABLE 1

Reducing Sugar Production by Enzymatic Hydrolysis of Irradiated Corn

Reducing Sugar (mg/g corn)

| Radiation (rd) | Untreated | Uncooked & amylases[b] | Cooked[a] & amylases[b] | Cooked[a] & α-amylase[c] | Cooked[a] & β-amylase[d] | Cooked[a] & amyloglucosidase[e] |
|---|---|---|---|---|---|---|
| 0 | 4.0 | 38.6 | 87.9 | 9.3 | 7.3 | 27.9 |
| $10^5$ | 4.0 | 25.3 | 143.8 | 6.7 | 6.7 | 31.9 |
| $10^6$ | 6.7 | 35.9 | 87.9 | 9.3 | 5.3 | 33.3 |
| $10^7$ | 8.6 | 42.6 | 139.8 | 12.0 | 10.6 | 38.6 |
| $5 \times 10^7$ | 37.3 | 119.9 | 163.8 | 29.3 | 58.6 | 100.0 |
| $10^8$ | 61.3 | 123.9 | 171.8 | 47.9 | 90.6 | 131.8 |

[a]10 g corn in 100 ml of water was heated at 121 C. for 30 min.
[b]A mixture of α-amylase (833 U), β-amylase (200 U) and amyloglucosidase (333 U) was added to 10 g corn in 100 ml $H_2O$. The enzyme-substrate mixture was held at 50° C. for 1 hr with occasional checking.
[c]Corn treated with α-amylase (833 U) as described in b.
[d]Corn treated with β-amylase (200 U) as described in b.
[e]Corn treated with amyloglucosidase (333 U) as described in b.

TABLE 2

Glucose Production by Enzymatic Hydrolysis[a] of Irradiated Corn

| Radiation (rd) | Untreated | Uncooked & amylases | Cooked & amylases | Cooked & α-amylase | Cooked & β-amylase | Cooked & amyloglucosidase |
|---|---|---|---|---|---|---|
| 0 | 2.53 | 28.6 | 76.6 | 10.6 | 3.46 | 26.6 |
| $10^5$ | 2.53 | 26.6 | 81.2 | 5.8 | 4.26 | 28.6 |
| $10^6$ | 2.66 | 31.9 | 83.9 | 5.3 | 4.79 | 28.6 |
| $10^7$ | 2.66 | 32.6 | 101.9 | 5.3 | 5.33 | 30.6 |
| $5 \times 10^7$ | 4.39 | 105.2 | 113.8 | 5.3 | 4.26 | 95.9 |
| $10^8$ | 4.66 | 106.5 | 115.2 | 5.3 | 3.73 | 99.2 |

Glucose (mg/g corn)

[a]Conditions for cooking and enzymatic hydrolysis were the same as noted in Table I.

TABLE 3

Yeast Growth on Irradiated Corn

| Radiation (rd) | Untreated | Uncooked & amylases[b] | Cooked[a] & amylases[b] |
|---|---|---|---|
| 0 | $9 \times 10^7$ | $20 \times 10^7$ | $21 \times 10^7$ |
| $10^5$ | $15 \times 10^7$ | $34 \times 10^7$ | $29 \times 10^7$ |
| $10^6$ | $13 \times 10^7$ | $34 \times 10^7$ | $22 \times 10^7$ |
| $10^7$ | $16 \times 10^7$ | $65 \times 10^7$ | $23 \times 10^7$ |
| $5 \times 10^7$ | $0 \times 10^6$ | $28 \times 10^7$ | $3 \times 10^7$ |
| $10^8$ | $0 \times 10^6$ | $10 \times 10^7$ | $5 \times 10^7$ |

Yeast Growth (cells/ml)

[a]Ten g corn in 100 ml $H_2O$ was heated at 121° C. for 30 min.
[b]A mixture of α-amylase (833 U), β-amylase (200 U) and amyloglucosidase (333 U) was added to 10 g corn in 100 ml $H_2O$. The enzymatic-substrate mixture was held at 50° C. for one hr. with occasional shaking.

TABLE 4

Iodine Affinity of Irradiated Corn

| Radiation (rd) | Iodine affinity (OD 580 nm) |
|---|---|
| 0 | 64.0 |
| $10^5$ | 70.0 |
| $10^6$ | 70.0 |
| $10^7$ | 65.0 |
| $5 \times 10^7$ | 18.0 |
| $10^8$ | 1.0 |

TABLE 5 pH and Titratable Acidity of Irradiated Corn

| Radiation (rd) | pH | Acidity[a] (mg $CH_3COOH$/100 g sample) |
|---|---|---|
| 0 | 5.4 | 0.26 |
| $10^5$ | 5.3 | 0.26 |
| $10^6$ | 5.3 | 0.26 |
| $10^7$ | 4.7 | 0.35 |
| $5 \times 10^7$ | 4.3 | 0.45 |
| $10^8$ | 4.1 | 0.81 |

[a]Ten g corn was suspended in 100 ml of $H_2O$ and shaken for one hr at room temperature. An aliquot was titrated using 0.01 N NaOH solution and acidity was calculated as mg of $CH_3COOH$ per 100 g of sample.

TABLE 6

Alcohol Production from Irradiated Corn (10%, w/v)

| Radiation (Rad) | Corn concentration (w/v) | Untreated | Uncooked and amylase treated[a] | Cooked and amylase treated[b] |
|---|---|---|---|---|
| 0 | 10% | 0.20 | 1.24 | 3.28 |
| $10^5$ | " | 0.20 | 3.51 | 3.38 |
| $10^6$ | " | 0.25 | 3.79 | 3.42 |
| $10^7$ | " | 0.16 | 2.99 | 3.32 |
| $5 \times 10^7$ | " | 0.14 | 2.88 | 3.04 |
| $10^8$ | " | 0.15 | 2.27 | 2.66 |
| 0 | 15% | 0.45 | 2.46 | 3.89 |
| $10^5$ | " | 0.13 | 3.30 | 4.09 |
| $10^6$ | " | 0.07 | 3.68 | 3.90 |
| $10^7$ | " | 0.17 | 2.26 | 3.80 |
| $5 \times 10^7$ | " | 0.78 | 3.36 | 3.49 |
| $10^8$ | " | 0.11 | 2.48 | 2.88 |
| 0 | 30% | 0.59 | 4.40 | 7.76 |
| $10^5$ | " | 0.50 | 4.56 | 8.79 |
| $10^6$ | " | 0.77 | 7.35 | 9.39 |
| $10^7$ | " | 0.65 | 4.40 | 9.29 |
| $5 \times 10^7$ | " | 0.32 | 7.23 | 8.33 |
| $10^8$ | " | 0.31 | 5.58 | 5.89 |

Alcohol (%, v/v)

[a]A mixture of α-amylase (833 U), β-amylase (200 U), and amyloglucosidase (333 U) was added to 30 g corn in 100 ml $H_2O$. The enzyme-substrate mixture was held at 50 C. for one hr with occasional shaking.
[b]Cooked (121 C., 30 min) corn was treated as described in a.

I claim:

1. An alcohol fermentation process which eliminates the heat gelatinization process comprising:
   (a) irradiating a starch based substrate with a sufficient amount of gamma radiation to effect sugar yield, susceptibility to enzymatic hydrolysis of starch, yeast growth, and alcohol production;
   (b) treating the irradiated starch based substrate with a sufficient amount of amylases complex to effect enzymatic action;
   (c) adding sufficient yeast to ferment the product of (b).

2. The process of claim 1 wherein the starch based substrate is corn.

3. The process of claim 2 wherein the amount of radiation used is from about $10^5$ to $10^7$ rad.

4. The process of claim 3 including a step of distillation of the fermented corn to produce alcohol.

* * * * *